United States Patent [19]

Imai et al.

[11] Patent Number: 4,795,843

[45] Date of Patent: Jan. 3, 1989

[54] CONVERSION OF METHANE INTO LARGER ORGANIC HYDROCARBONS

[75] Inventors: Tamotsu Imai, Mt. Prospect; Paul T. Barger, Arlington Heights; Anthony H. Eck, Chicago, all of Ill.

[73] Assignee: UOP Inc., Des Plaines, Ill.

[21] Appl. No.: 105,930

[22] Filed: Oct. 8, 1987

Related U.S. Application Data

[63] Continuation-in-part of Ser. No. 768,983, Aug. 26, 1985, abandoned.

[51] Int. Cl.$^4$ .................... C07C 11/20; C07C 11/32; C07C 1/00
[52] U.S. Cl. ................................. 585/408; 585/359; 585/469; 585/642; 585/733
[58] Field of Search ............... 585/359, 408, 469, 642, 585/733

[56] References Cited

U.S. PATENT DOCUMENTS

| | | | |
|---|---|---|---|
| 2,488,083 | 11/1949 | Gorin et al. | 585/642 |
| 3,894,105 | 7/1975 | Chang et al. | 585/408 |
| 4,384,159 | 5/1983 | Diesen | 585/642 |
| 4,524,234 | 6/1985 | Kaiser | 585/733 |
| 4,579,996 | 4/1986 | Fontfreide et al. | 585/733 |

*Primary Examiner*—Curtis R. Davis
*Attorney, Agent, or Firm*—Thomas K. McBride; Raymond H. Nelson

[57] ABSTRACT

Organic hydrocarbons which comprise useful compounds may be obtained in a two-step process utilizing methane as a feedstock. The desired compounds are prepared by treating said methane with a halogenating agent such as chlorine, followed by contacting the methyl halide with a conversion catalyst comprising a silicalite. The silicalite which is employed is a silica polymorph consisting of crystalline silica which, after calcination in air at a temperature of 600° C. for 1 hour, has a mean refractory index of 1.39±0.01 and a specific gravity at 25° C. of 1.70±0.05 g/cc.

12 Claims, No Drawings

CONVERSION OF METHANE INTO LARGER ORGANIC HYDROCARBONS

CROSS REFERENCE TO RELATED APPLICATION

This application is a continuation-in-part of our co-pending application Ser. No. 768,983 filed Aug. 26, 1985, and now abandoned all teachings of which are incorporated herein by reference thereto.

BACKGROUND OF THE INVENTION

Natural gas which comprises a mixture of gases including methane, ethane and propane is a by-product of oil recovery from subterranean reservoirs. The presence of these gases at the well site or possibly as by-products from petroleum refining operations constitutes an undesirable element inasmuch as a necessity is present for recovery of these gases in an economical and safe manner. Therefore, there is a need at these sites to provide some process for transporting this material away from the well site or refinery site in such a manner so that it is possible to utilize these gases in a commercially attractive manner. One method which has been employed in recovering an oversupply of a low carbon content gas such as methane is to convert the methane into methyl alcohol. However, the conversion of methane into methyl alcohol possesses some inherent disadvantages inasmuch as the process for the conversion requires several steps. After obtaining the alcohol, it is then necessary to convert this alcohol into other products.

Another method of treating the unwanted low molecular weight gases is to convert said gases into a halide. For example, it is relatively easy and inexpensive to convert methane into methyl chloride using existing technology which involves conversion processes. This conversion step to the organic halide can be readily accomplished at a well site or refinery site. However, the resulting organic halide must then be converted into usable, easily transportable products for further use in the chemical industry. Examples of usable products which find a wide variety of use in the chemical field will include aromatic compounds such as benzene, toluene, the isomeric xylenes, ethylbenzene, etc. as well as straight or branched chain hydrocarbons containing 4 or more carbon atoms in the chain such as butane, butene, pentane, pentene, hexane, hexene, as well as the isomeric molecules, etc.

As will hereinafter be shown in greater detail, we have now discovered that methane may be treated with a halide agent to form a methyl halide following which the methyl halide may be converted into usable products by contacting said halides with a particular type of crystalline silica material. Prior U.S. patents have disclosed various methods for treating alkyl halides or other compounds to form desirable products. For example, U.S. Pat. No. 3,894,107 discloses a method for the conversion of alcohols, mercaptans, sulfides, halides, and/or amines to form desirable compounds. However, the catalyst which is utilized to effect this conversion comprises a particular type of a crystalline aluminosilicate catalyst which, as will hereinafter be set forth in greater detail, differs in many respects from the catalyst which is used to effect the process of the present invention. U.S. Pat. Nos. 3,894,105 and 4,524,234 teach a method for the conversion of compounds such as methyl chloride. However, these patents do not suggest such conversion is accomplished in the presence of the particular silicalite catalyst which is used in the present invention. U.S. Pat. No. 2,488,083 is directed to a process for the manufacture of liquid hydrocarbons by the condensation of alkyl halides in a dehydrohalogeno-condensation reaction. However, the inventive concept of this patent resides in the use of a diluent such as $C_2$ to $C_4$ hydrocarbons produced during the reaction in the reaction zone. The presence of such diluents enhances the liquid hydrocarbon content of the product which is a fact conformed by both the examples and the specification of this patent. U.S. Pat. No. 4,579,996 teaches the conversion of methyl chloride over a catalyst comprising a clay which contains either hydrogen ions and/or metal cations which have been introduced into the catalyst either by exchange and/or by deposition. Table 1 of this patent indicates that the methyl chloride is converted primarily to hydrocarbons containing from 1 to 5 carbon atoms.

U.S. Pat. No. 4,384,159 discloses a process for treating saturated hydrochlorocarbons containing from 1 to 6 carbon atoms with a silicalite catalyst in a dehydrochlorination process to form olefinic compounds. The dehydrochlorination process which is effected in this patent relates to the elimination of the constituents of hydrogen chloride from adjacent carbon atoms of an alkyl halide to afford a carbon-carbon double or triple bond. This is an art-recognized reaction which does not provide for an increase in the number of carbon atoms in the products compared with the reactants. The examples present in this reference describe the production of olefinic products such as vinylchloride and ethylene from ethylene dichloride, ethylene from ethyl chloride, and 1,2-dichloroethylene from 1,1,2-trichloroethane.

As will hereinafter be set forth in greater detail, in contrast to the sample dehydrochlorination process which is described in U.S. Pat. No. 4,384,159 and as exemplified by reactants containing 2 carbon atoms, we have unexpectedly discovered that by forming a methyl halide from methane and contacting the resultant methyl halide with the silicalite catalyst of the present invention will result in the formation of products which are distinctly different from those described by this patent. Instead of resulting in the formation of hydrocarbon products which possess a carbon atom number corresponding to the feedstock, we will form paraffins, olefins, and aromatic products containing from 2 to 8 or more carbon atoms in the product, the production being produced from a feedstock containing a single carbon atom.

The formation of such products by utilizing the process of this invention may involve several reaction mechanisms including condensation reactions which combine small molecules into larger ones; oligomerization which is the combination of small molecules into larger molecules without the loss of a simple molecule; cyclization, which is the production of a compound containing a ring derived from an acyclic molecule having the same number of carbon atoms; aromatization, which is the conversion of small hydrocarbons into aromatic compounds and may include such steps as oligomerization, cyclization, and dehydrocyclization (cyclization accompanied by the loss of hydrogen), or alkylation, in which an alkyl side chain is attached to an aromatic ring.

BRIEF SUMMARY OF THE INVENTION

This invention relates to a two-step process for converting a feestock comprising methane into methyl halide and thereafter converting this methyl halide into hydrocarbons containing a larger number of carbon atoms than was possessed by the original feedstock. More particularly, the invention is concerned with a process for converting methane into more usable chemical compounds.

As was previously set forth, the presence of off-gases or natural gases which are present at well sites or petroleum refining sites constitute an unwanted element. It is therefore necessary to convert these unwanted compounds into more useful chemical products which are easily transportable from the site where the gases are produced. Among the more useful organic products which may be obtained by the process of the present invention are aromatic hydrocarbons. These aromatic hydrocarbons are important chemical compounds which find a wide variety of uses in industry as a whole. For example, benzene may be used as an intermediate in the production of styrene, phenol, synthetic detergents as well as being used to produce products which are useful as insecticides, fumigants, etc. Likewise, toluene is used as a solvent for paints, coatings, and rubber cement, in aviation gasoline and high octane blending stock, in medicines, dyes, perfumes, etc. In addition to producing aromatic compounds as one of the useful products obtained by the process of the present invention, it is also possible to prepare aliphatic hydrocarbons such as butane, which is used as a raw material for synthetic rubber and high octane liquid fuels; as a fuel for household and industrial purposes; as a solvent, refrigerant, aerosol, propellant, etc. Likewise, pentane will find a use as an anesthetic, as a solvent in solvent extraction processes, in the manufacture of artificial ice, etc. It is therefore readily apparent gases containing from 1 to about 3 carbon atoms which are present in natural gas or as the off-shoot of oil recovery of petroleum refining processes may be converted into many useful products.

It is therefore an object of this invention to provide a process for converting unwanted gaseous by-products into useful compounds.

A further object of this invention is found in a process for converting unwanted or undesirable gases into useful chemical compounds utilizing, as a catalyst therefore, a particular type of crystalline material.

In one aspect, an embodiment of this invention resides in a process for the production of aliphatic and aromatic hydrocarbons containing more than one carbon atom which comprises the steps of: (a) treating methane with a haliding agent at haliding conditions; (b) contacting the resultant methyl halide with a catalyst comprising a silica polymorph consisting of crystalline silica, said silica polymorph after calcination in air at 600° C. for a period of one hour having a mean refractory index of 1.39±0.01 and a specific gravity at 25° C. of 1.70±0.005 g/cc at conversion conditions; and (c) recovering the resultant aliphatic and aromatic hydrocarbons.

A specific embodiment of this invention is found in a process for treating methane with chlorine at a temperature in the range of from about 150° to about 550° C. and a pressure in the range of from about atmosphere to about 100 atmospheres, contacting the resultant methyl chloride with a catalyst comprising a silica polymorph consisting of crystalline silica, said silica polymorph after calcination in air at 600° C. for a period of 1 hour having a mean refractory index of 1.39±0.01 and a specific gravity at 25° C. or 1.70±0.05 g/cc at a temperature in the range of from about 100° to about 900° C., a pressure in the range of from about 0.1 to about 100 atmospheres and a liquid hourly space velocity in the range of from about 0.1 to about 50 hrs$^{-1}$, and recovering the resultant aliphatic hydrocarbons which comprise a mixture of hydrocarbons containing from 2 to about 5 carbon atoms, and aromatic hydrocarbons which comprise a mixture of benzene, toluene, ethylbenzene, and isomeric xylenes.

Other objects and embodiments will be found in the following detailed description of the invention.

DETAILED DESCRIPTION OF THE INVENTION

As hereinbefore set forth, the present invention is concerned with a process for converting methane into organic compounds which contain a greater number of carbon atoms. The process is effected by treating methane with a haliding agent at haliding conditions to form the corresponding methyl halide. Examples of haliding agents which may be employed include chlorine, bromine and iodine. It is also contemplated that the haliding agent which is employed in the present process may also comprise fluorine, although not necessarily with equivalent results. Haliding conditions which are utilized to obtain the desired methyl halide and include temperatures in the range of from about 150° to about 550° C. and a pressure in the range of from about atmospheric to about 100 atmospheres. In the present embodiment of the invention the haliding reaction is effected in a thermal process, although it is also contemplated that the desired methyl halide may be obtained by employing photochemical or catalytic processes. In the preferred embodiment of the invention the extent of halogenation of methane in the desired product is accomplished by varying the halogen to methane feed ratio, the product of a monohalo-substituted methane being maximized by using halogen to methane feed ratio of less than 1.0. In addition, it is also contemplated that temperatures below about 450° C. are preferred in order to minimize or prevent the formation of carbon. The desired halogenation of the methane may be accomplished in either a batch or continuous type operation and the product which is obtained from this reaction may be subjected to fractional distillation whereby the methyl monohalide may be separated from any methyl di-, tri-, or tetrahalide. This separation is desired inasmuch as little or no conversion of the polyhalo-substituted methane will be achieved when utilizing the conversion conditions and the catalyst of the present invention. The differences in conversion of a monohalo-substituted methane and a polyhalo-substituted methane will be hereinafter shown in greater detail.

The methyl halide which has been recovered is then contacted with a catalyst comprising a silica polymorph consisting of crystalline silica. As was previously discussed, organic compounds which contain, in addition to the carbon and hydrogen, other atoms such as sulfur, halogen, oxygen, etc. have been converted to desirable products utilizing as a catalyst for the conversion a particular type of crystalline aluminosilicate catalyst. These catalysts comprise crystalline aluminosilicate zeolites having a particular crystal structure. These types of zeolites are commercially referred to as ZSM- 5, ZSM-11, ZSM-12, ZSM-21, etc. The preparation of these catalysts is described in various U.S. Pat. Nos. such as 3,702,886.

In contradistinction to the use of the crystalline aluminosilicate zeolites which have been thus described and utilized as a catalyst in U.S. Pat. No. 3,894,107 hereinbefore set forth, we have now discovered that organic halides of the type hereinafter set forth in greater detail will be converted to usable products by contacting these halides with a crystalline silica composition which is hereinafter referred to as silicalite. This composition is utilized and claimed in U.S. Pat. No. 4,061,724. As was discussed in this patent, the crystalline silica composition differs from crystalline aluminosilicate compositions in that while exhibiting molecular sieve properties which are characteristic of the latter composition exhibits none of the ion-exchange properties which are essential to the zeolitic molecular sieves.

The crystalline silica polymorph which is used as a catalyst for the process of the present invention will possess certain properties. These properties which are present in the composition which, after having been calcined in air at a temperature of 600° C. for one hour, will include a specific gravity at 25° C. of 1.7 grams ±0.05 g/cc and a mean refractive index of 1.39±0.01. In addition, the composition will also have an X-ray powder diffraction pattern similar in nature to that which is set forth in tables A and B of the aforementioned U.S. Pat. No. 4,061,724. As will hereinafter be shown in greater detail, the use of such a catalyst comprising silicalite will result in a significantly improved stability of the catalyst when compared to the other catalysts such as the aforementioned aluminosilicate molecular sieve catalysts.

The methyl halide, such as methyl chloride, methyl bromide, methyl iodide, or methyl fluoride, which has been recovered from the fractional distillation, is converted to usable products by contact with a crystalline silica polymorph of the type hereinbefore set forth in conversion conditions which will include temperatures ranging from about 100° to 900° C., pressures ranging from about 0.1 to about 100 atmospheres, and Liquid Hourly Space Velocities ranging from about 0.1 to about 50 hrs.$^{-1}$.

The process of the present invention utilizing, as a catalyst for the conversion of organic halides into larger organic hydrocarbons, a silicalite may be effected in any suitable manner and may comprise either a batch or continuous type operation. For example, when a batch type operation is to be employed, the silicalite catalyst which may be in various physical forms or shapes including spheres, pellets, granules, powders, extrudates, spray-dried particles, etc. is placed in an appropriate apparatus such as a flask or a pressure-resistant autoclave. The methyl halide is charged to the reaction apparatus which is then heated to the desired operating temperature and pressurized to the desired operating pressure. The conversion reaction is allowed to proceed for a period of time which may range from about 0.5 up to about 10 hours or more in duration. At the end of the reaction period, heating is discontinued and after the reaction apparatus has returned to room temperature, any excess pressure which may be present is discharged and the reaction mixture is recovered from the apparatus. This mixture may then be subjected to various separation processes such as fractional distillation under reduced pressure whereby the various organic compounds which contain a greater amount of carbon atoms than did the original feedstock are separated and recovered.

It is also contemplated within the scope of this invention that the conversion reaction may be effected in a continuous manner of operation. When such a type of operation is employed, the silicalite catalyst is positioned in an appropriate apparatus which is maintained at the proper operating conditions of temperature and pressure and the methyl halide is continuously charged to the reactor. Upon completion of the desired residence time in the reaction apparatus and the contact with the catalyst, the reactor effluent is continuously discharged and subjected to separation means whereby the desired organic compounds may be separated into their various components as well as being separated from any unreacted feedstock, the latter then being recycled back to the reaction zone to form a portion of the feed charge.

The continuous type of operation may be effected in various ways. For example, one type of continuous operation which may be employed comprises the fixed bed type of operation in which the catalyst is positioned as a fixed bed in the reaction apparatus and the feedstock is contacted with the catalyst in either an upward or downward flow. Another type of operation which may be employed comprises the moving bed type of operation in which the catalyst bed and the feedstock are passed through the reaction zone either concurrently or countercurrently to each other. Other types of operations which may also be used include the fluidized type of bed or the slurry type in which the catalyst is carried into the reaction zone as a slurry.

Examples of various types of organic compounds which may be produced by the conversion process of the present invention will include ethane, ethylene, propane, propylene, butane, butylene, the isomeric pentanes, pentenes, hexanes, hexenes, heptanes, heptenes, octanes, octenes, cyclopropene, cyclopropane, cyclobutene, cyclobutane, cyclopentene, cyclopentane, cyclohexene, cyclohexane, benzene, toluene, xylene, etc.

The following examples are given for purposes of illustrating the process of the present invention utilizing a silicalite catalyst. However, it is to be understood that these examples are given merely for purposes of illustration and that the present invention is not necessarily limited thereto.

EXAMPLE I

A halogenating agent comprising chlorine gas is injected into a feedstream comprising methane at an elevated temperature, said elevated temperature being sufficient so that the maximum temperature upon reaction does not exceed 400° C. The reaction is effected in a stainless steel tube provided with internal baffles which facilitate a thorough admixture of the reactants. The pressure during the reaction may be maintained at about 3.5 atmospheres. In order to maximize the formation of a monochlorinated product, the ratio of methane to chlorine is greater than 1, the gaseous hourly space velocity which is employed being sufficient to ensure a complete conversion of chlorine, the reactor effluent is withdrawn and subjected to fractional distillation whereby the desired methyl chloride is separated from any polychlorinated byproducts which may be formed as well as any hydrogen chloride which is formed.

A silicalite catalyst which possesses the desired properties of specific gravity and mean refractive index hereinbefore set forth which was utilized in the conversion process of the present invention was prepared by washing silicalite powder with nitric acid followed by oil dropping the powder in an aluminum phosphate solution. The resulting catalyst was then calcined in an atmosphere comprising 98% nitrogen and 2% oxygen for a period of one hour at a temperature of 350° C. followed by a period of two hours at 550° C. and three hours in an air atmosphere at the latter temperature. The recovered catalyst was then calcined in a steam atmosphere for a period of two hours at 600° C. and recovered, said catalyst having 67% silicalite and an Apparent Bulk Density of 0.509 g/cc. The catalyst was then placed in a Vycor fixed bed reactor which was heated by a three-zone furnace. The feedstock comprising a mixture of methyl chloride and nitrogen was charged to the reactor at a Liquid Hourly Space Velocity of 1.39 hrs.$^{-1}$ while maintaining an inlet temperature of 400° C. and atmospheric pressure. The reaction was run for a period of six hours during which time the conversion of the methyl chloride was maintained at 100%.

In contrast to this, a crystalline aluminosilicate catalyst which did not possess the properties of the silicalite catalyst and which had been prepared in a similar manner, that is, washed with nitric acid, oil dropped, followed by washing with ammonium nitrate and calcination at similar temperatures and atmospheres was used in a similar manner as a catalyst for the conversion of methyl chloride. The conditions which were employed for this second test were identical to those described in the above paragraph. The test was effected for a period of five hours during which time the conversion of the methyl chloride dropped from about 98% to about 71%. This indicated the stability of the silicalite catalyst in terms of conversion of the feedstock as compared to the crystalline aluminosilicate catalyst.

EXAMPLE II

In this example, a silicalite catalyst and a crystalline aluminosilicate catalyst which were prepared in a manner similar to that set forth in Example I above were utilized for the conversion of methyl chloride. The conversion reaction was effected to a charge of methyl chloride and nitrogen to the reactor at a Liquid Hourly Space Velocity of 1.39 hours$^{-1}$, atmospheric pressure, and an inlet temperature of 300° C. At the end of the six-hour period, the conversion of methyl chloride while using the silicalite catalyst was 100%. In contrast to this, the conversion of methyl chloride when using the crystalline aluminosilicate catalyst dropped from 25% at two hours to 15% at three hours, at which time the test was discontinued.

EXAMPLE III

To illustrate the efficacy of the silicalite catalyst of the present invention with regard to the stability and rate of conversion of the methyl halide, a series of tests were run utilizing various catalysts. The catalysts which were employed comprised silicalite (A), an amorphous aluminosilicate (B), a Y zeolite (C), a mordenite (D), and a crystalline aluminosilicate having about a 20:1 ratio of silica to alumina (E).

TABLE 1

| | A | B | C | D | E |
|---|---|---|---|---|---|
| Catalyst | | | | | |
| Hrs. on Stream | 1 | 1 | 1 | 1 | 1 |
| Temperature, °C. | 400 | 500 | 500 | 500 | 400 |
| Pressure, psig | 1.5 | 0 | 0 | 0 | 1.8 |
| LHSV (hrs.$^{-1}$) | 1.02 | 1.52 | 1.45 | 1.46 | 1.39 |
| Methyl Chloride conversion % | 100 | 16.6 | 83.9 | 69.9 | 98.5 |
| Mole % Selectivities | | | | | |
| $C_2+$ | 98.3 | 59 | 10.9 | 18.0 | 97.2 |
| Aromatics | 5.8 | 0 | 0 | 0 | 24.9 |
| $C_1$ | 1.7 | 41 | 89.1 | 82 | 2.8 |
| $C_2$ | .3 | 2.4 | 3 | 3.1 | 2.6 |
| $C_2=$ | 6.3 | 7.2 | 4.3 | 5.7 | 2.3 |
| $C_3$ | 8.4 | 0 | 1.9 | .8 | 49 |
| $C_3=$ | 17.3 | 7.2 | .6 | 3.1 | 2.5 |
| $C_4$ | 13.1 | 0 | 0 | 0 | 12 |
| $C_4=$ | 14.8 | 0 | 0 | 0 | .6 |
| $C_5+$ | 32.3 | 42.2 | 1.1 | 5.0 | .32 |
| Benzene | .4 | 0 | 0 | 0 | .4 |
| Toluene | 2.0 | 0 | 0 | 0 | 4.1 |
| Ethylbenzene | .2 | 0 | 0 | 0 | .1 |
| o-Xylene | .2 | 0 | 0 | 0 | 2.6 |
| m-Xylene | .3 | 0 | 0 | 0 | 5.9 |
| p-Xylene | 1.7 | 0 | 0 | 0 | 2.7 |
| Others | 1 | 0 | 0 | 0 | 9.1 |

It is to be noted that the use of catalysts B, C, and D resulted in a relatively low conversion of the methyl chloride with a high percentage of methane and no aromatic production. While the use of catalyst E resulted in a high aromatic production as well as a high nonaromatic production, the stability of this catalyst as set forth in Examples I and II above was poor and resulted in a drop-off of conversion after a period of one hour when compared to the silicalite catalyst of the present invention.

EXAMPLE IV

To illustrate the necessity for treating a monohalo-substituted methane with the silicalite catalyst of the present invention as contrasted with polyhalo-substituted methane, three tests were conducted using a methylene chloride ($CH_2Cl_2$) as a feedstock which was contacted with a catalyst comprising a silicalite prepared according to the method set forth in Example I above. The three tests were conducted at temperatures of 300°, 400° and 500° C. in an manner similar to that set forth in the above examples. The results of these test showed that there was no appreciable conversion of the methylene chloride when utilizing reaction temperatures of 300° and 400° C. At 500° C. approximately 47% of the methylene chloride was converted to various products comprising primarily coke (98 weight percent) and small amounts of light organic chlorides such as methyl chloride (0.2 weight percent), chloroethane (trace), dichloroethane (0.4 weight percent), chloroform (1.1 weight percent). These tests indicate that methylene chloride which is a di-substituted saturated chloride is not successfully converted into any appreciable amount of useful products.

This is in contrast to methyl chloride, a mono-substituted saturated chloride, which is completely converted to various products at 300° C. and 400° C. as evidenced by Examples I and II. Furthermore, run A of Example III demonstrates that the methyl chloride is completely converted at 400° C. into various products comprising 98.3% of $C_2+$hydrocarbons and 5.8% of aromatics.

We claim as our invention:
1. A process for the production of aliphatic and aromatic hydrocarbons containing more than one carbon atom which comprises contacting at conversion conditions a feedstock containing methyl halide with a catalyst comprising a silica polymorph consisting of crystalline silica, said silica polymorph after calcination in air at 600° C. for one hour having a mean refractory index of 1.39±0.01 and a specific gravity at 25° C. of 1.70±0.05 g/cc, and recovering the resultant aliphatic and aromatic hydrocarbons.

2. The process as set forth in claim 1 in which said haliding conditions include a temperature in the range of from about 150° to about 550° C. and a pressure in the range of from about atmospheric to about 100 atmospheres.

3. The process as set forth in claim 1 in which said haliding agent comprises chlorine.

4. The process as set forth in claim 1 in which said haliding agent comprises bromine.

5. The process as set forth in claim 1 in which said haliding agent comprises iodine.

6. The process as set forth in claim 1 in which said conversion conditions include a temperature in the range of from about 100° to about 900° C., a pressure in the range of from about 0.1 to about 100 atmospheres and a liquid hourly space velocity in the range of from about 0.1 to about 50 hours$^{-1}$.

7. The process as set forth in claim 1 in which said methyl halide comprises methyl chloride.

8. A process as set forth in claim 1 in which said methyl halide comprises methyl bromide.

9. The process as set forth in claim 1 in which said methyl halide comprises methyl iodide.

10. The process as set forth in claim 1 in which said aromatic hydrocarbons comprise a mixture of benzene, toluene, ethylbenzene and isomeric xylenes.

11. The process as set forth in claim 1 in which said aliphatic hydrocarbons comprise a mixture of hydrocarbons containing from 2 to about 5 carbon atoms.

12. The process as set forth in claim 1 wherein said catalyst comprises said silica polymorph in an aluminum phosphate binder.

* * * * *